(12) United States Patent
Ishii et al.

(10) Patent No.: US 7,321,071 B2
(45) Date of Patent: Jan. 22, 2008

(54) PROCESS FOR THE PRODUCTION OF WATER-SOLUBLE FLUORINE-CONTAINING VINYL ETHERS

(75) Inventors: Kenji Ishii, Settsu (JP); Noriyuki Shinoki, Settsu (JP); Takuya Arase, Settsu (JP); Kazuyoshi Ichihara, Settsu (JP); Toshiya Mantani, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 11 days.

(21) Appl. No.: 10/517,667

(22) PCT Filed: Jun. 16, 2003

(86) PCT No.: PCT/JP03/07592

§ 371 (c)(1),
(2), (4) Date: Dec. 13, 2004

(87) PCT Pub. No.: WO03/106409

PCT Pub. Date: Dec. 24, 2003

(65) Prior Publication Data

US 2005/0245758 A1    Nov. 3, 2005

(30) Foreign Application Priority Data

Jun. 14, 2002 (JP) .............................. 2002-175130

(51) Int. Cl.
C07C 17/00 (2006.01)
C07C 17/25 (2006.01)
(52) U.S. Cl. ..................................................... 570/155
(58) Field of Classification Search ................ 568/687; 570/123, 134, 135, 136, 140, 142, 153, 155
See application file for complete search history.

(56) References Cited

U.S. PATENT DOCUMENTS 6,274,677 B1 * 8/2001 Tatemoto ..................... 525/276
6,649,790 B1 * 11/2003 Tatemoto ..................... 562/111

FOREIGN PATENT DOCUMENTS

| DE | 27 08 677 A1 | 8/1978 |
| EP | 0 041 738 | 12/1981 |
| EP | 41738 A1 | 12/1981 |
| EP | 1 026 152 A1 | 8/2000 |
| EP | 1 225 167 A1 | 7/2002 |
| WO | WO98/43952 | 8/1998 |
| WO | WO 01/28989 A1 | 4/2001 |

OTHER PUBLICATIONS

International Search Report for PCT/JP03/07592 dated Oct. 28, 2003.

* cited by examiner

*Primary Examiner*—Karl Puttlitz
(74) *Attorney, Agent, or Firm*—Sughrue Mion Pllc.

(57) ABSTRACT

The present invention relates to a method for producing a water-soluble fluorine-containing vinyl ether which comprises subjecting a fluorine-containing 2-alkoxypropionic acid derivative represented by the following general formula (I):

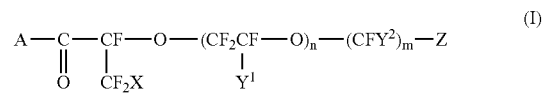

(wherein A represents $-OM^1$ or $-OM^2_{1/2}$, and $M^1$ represents an alkali metal and $M^2$ represents an alkaline earth metal; X represents a halogen atom; $Y^1$ and $Y^2$ are the same or different and each represents a fluorine atom, a chlorine atom, a perfluoroalkyl group or a fluorochloroalkyl group; n represents an integer of 0 to 3, and n of $Y^1$s may be the same or different; m represents an integer of 1 to 5, and m of $Y^2$s are the same or different; and Z represents a hydrophilic group) to thermal decomposition at a temperature of not lower than 50° C. but lower than 170° C. in the presence of a coordinating organic solvent to give a water-soluble fluorine-containing vinyl ether represented by the general formula (II):

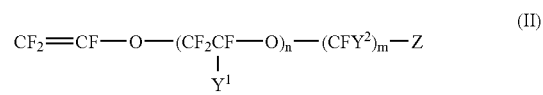

(wherein $Y^1$, $Y^2$, Z, n and m are as defined above),
said coordinating organic solvent having a coordinating property with an ion of said $M^1$ or an ion of said $M^2$
said coordinating organic solvent being in an amount of 10 to 1,000 parts by mass per 100 parts by mass of the fluorine-containing 2-alkoxypropionic acid derivative.

18 Claims, No Drawings

PROCESS FOR THE PRODUCTION OF WATER-SOLUBLE FLUORINE-CONTAINING VINYL ETHERS

CROSS-REFERENCE TO RELATED APPLICATION

This Application is 371 of PCT/JP03/07592 filed Jun. 16, 2003.

TECHNICAL FIELDS

The present invention relates to a method for producing a water-soluble fluorine-containing vinyl ether from fluorine-containing 2-alkoxypropionic acid derivatives in good yields.

BACKGROUND ART

Hydrophilic group-terminated fluorine-containing vinyl ethers can be used, either as such or after protection of the terminal hydrophilic group by fluorination or by esterification, amidation or imidation, for the production of copolymers by polymerization with another fluoroolefin and/or the like.

The copolymers obtained can have salt-forming hydrophilic groups and, therefore, the use thereof as ion exchange membranes in salt electrolysis, chemical sensors, separation membranes, fuel cells and so forth is under investigation. They can also be utilized as superstrong acid catalysts in the form of powders as such, or in lithium cells and so on.

As a method for obtaining water-soluble fluorine-containing vinyl ethers, there is disclosed, in WO 98/43952 pamphlet, a thermal decomposition method which comprises heating, for decarboxylation, a fluorine-containing 2-alkoxypropionic acid derivative with carboxyl group being in the form of a metal salt. This thermal decomposition method known in the art has a problem in that a side reaction occurs, namely oligomers are formed from the fluorine-containing 2-alkoxypropionic acid derivative.

As regards the reaction conditions for this thermal decomposition, WO 01/28989 pamphlet discloses that the reaction should preferably be carried out at 170 to 230° C. using 1 to 5 parts by weight of a catalyst having a coordinating property with a metal ion per 100 parts by weight of the fluorine-containing 2-alkoxypropionic acid derivative.

Under such conditions, however, the byproduct oligomers are formed in large amounts and the yield of the desired product thus decreases. In carrying out the reaction on a large scale using a large-sized reactor, in particular, a long time is required for raising the temperature and for lowering the temperature, whereby the production of oligomers further increases. Thus, there is a problem that such conditions are difficult to apply on a commercial scale.

The water-soluble fluorine-containing vinyl ethers, which are the target products to be obtained by this thermal decomposition reaction, occur as high-boiling salts and, therefore, the distillation method cannot be used as the method of purifying them. A promising method is recrystallization. However, it is not easy to crystallize the water-soluble fluorine-containing vinyl ethers in the presence of a large amount of oligomers, which are uncrystallizable and thus render the purification by recrystallization difficult to achieve.

SUMMARY OF THE INVENTION

In view of the above-discussed state of the art, it is an object of the present invention to provide a method for producing a water-soluble fluorine-containing vinyl ether in good yields from fluorine-containing 2-alkoxypropionic acid derivatives.

The present invention relates to a method for producing a water-soluble fluorine-containing vinyl ether which comprises subjecting a fluorine-containing 2-alkoxypropionic acid derivative represented by the following general formula (I):

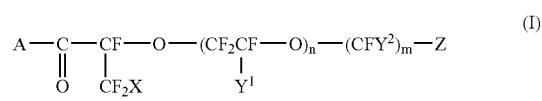

(wherein A represents —OM$^1$ or —OM$^2_{1/2}$, and M$^1$ represents an alkali metal and M$^2$ represents an alkaline earth metal; X represents a halogen atom; Y$^1$ and Y$^2$ are the same or different and each represents a fluorine atom, a chlorine atom, a perfluoroalkyl group or a fluorochloroalkyl group; n represents an integer of 0 to 3, and n of Y$^1$s may be the same or different; m represents an integer of 1 to 5, and m of Y$^2$s are the same or different; and Z represents a hydrophilic group) to thermal decomposition at a temperature of not lower than 50° C. but lower than 170° C. in the presence of a coordinating organic solvent to give a water-soluble fluorine-containing vinyl ether represented by the following general formula (II):

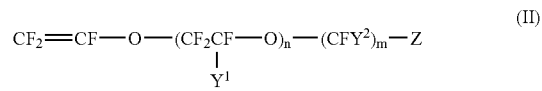

(wherein Y$^1$, Y$^2$, Z, n and m are as defined above),
said coordinating organic solvent having a coordinating property with an ion of said M$^1$ or an ion of said M$^2$ and
said coordinating organic solvent being used in an amount of 10 to 1,000 parts by mass per 100 parts by mass of the fluorine-containing 2-alkoxypropionic acid derivative.

In the following, the present invention is described in detail.

DETAILED DISCLOSURE OF THE INVENTION

The method for producing a water-soluble fluorine-containing vinyl ether comprises subjecting a fluorine-containing 2-alkoxypropionic acid derivate represented by the above general formula (I) to thermal decomposition.

The fluorine-containing 2-alkoxypropionic acid derivative represented by the above general formula (I) is such one that A in the above general formula (I) represents —OM$^1$ or —OM$^2_{1/2}$, wherein M$^1$ represents an alkali metal and M$^2$ represents an alkaline earth metal. The alkali metal M$^1$ is not particularly restricted but includes, among others, Li, Na, K and Cs. The alkaline earth metal M$^2$ is not particularly restricted but includes, among others, Mg and Ca. Preferably, A is —OM$^1$, and M$^1$ is Na, which is commercially inexpensive.

In the above general formula (I), X represents a halogen atom. The halogen atom is not particularly restricted but may be any of fluorine, chlorine, bromine and iodine atoms.

In the above general formula (I), $Y^1$ and $Y^2$ are the same or different and each represents a fluorine atom, a chlorine atom, a perfluoroalkyl group or a fluorochloroalkyl group. The perfluoroalkyl group is not particularly restricted but maybe, for example, a trifluoromethyl group or a pentafluoroethyl group. The fluorochloroalkyl group is not particularly restricted but may be, for example, a difluorochloromethyl group. Preferably, $Y^1$ is a trifluoromethyl group and $Y^2$ is a fluorine atom.

In the above general formula (I), n represents an integer of 0 to 3. The n of $Y^1$s may be the same or different. For the fluorine-containing 2-alkoxypropionic acid derivative having a lot of hydrophilic groups per unit weight thereof, the above-mentioned n is preferably 0 or 1, more preferably 0.

In the above general formula (I), m represents an integer of 1 to 5. The m of $Y^2$s may be the same or different. As the above-mentioned m increases, the acid strength increases but the number of the hydrophilic groups per unit weight of the fluorine-containing 2-alkoxypropionic acid derivative decreases. Therefore, the above-mentioned m is preferably 2.

In the above general formula (I), Z represents a hydrophilic group. The hydrophilic group is not particularly restricted but may be, for example, —COOM$^3$, —OSO$_3$M$^3$, —SO$_3$M$^3$, —O$_2$PM$^3$, —OP (OM$^3$)$_2$, —O$_2$P (OM$^3$), —OPO (OM$^3$)$_2$, —PO$_2$ (OM$^3$), —PO(OM$^3$)$_2$, —COOM$^4{}_{1/2}$, —OSO$_3$M$^4{}_{1/2}$, —SO$_3$M$^4{}_{1/2}$, —O$_2$PM$^4{}_{1/2}$, —OP (OM$^4{}_{1/2}$)$_2$, —O$_2$P (OM$^4{}_{1/2}$), —OPO (OM$^4{}_{1/2}$)$_2$, —PO$_2$ (OM$^4{}_{1/2}$), —PO (OM$^4{}_{1/2}$)$_2$, or a substituted ammonio group forming a salt with a conjugate base of an inorganic acid or fatty acid (its substituents being two or three alkyl groups which may be the same or different).

The above-mentioned M$^3$ represents an alkali metal or hydrogen atom or NR$^1$R$^2$R$^3$R$^4$, and R$^1$, R$^2$, R$^3$ and R$^4$ are the same or different and each represents a hydrogen atom or an alkyl group containing 1 to 4 carbon atoms. The alkali metal includes, among others, those given above by way of example referring to M$^1$. The above-mentioned M$^4$ is an alkaline earth metal, and the alkaline earth metal includes, among others, those given above by way of example referring to M$^2$.

The term "substituted ammonio group" as used herein means a group constituted of a nitrogen atom and two or three alkyl groups, which are the same or different and are covalently bound to that nitrogen atom at sites other than the site represented by —(CFY$^2$)$_m$— in the above general formula (I).

The substituted ammonio group is not particularly restricted but may be —NR$^5$R$^6$H or —NR$^5$R$^6$R$^7$ (in which R$^5$, R$^6$ and R$^7$ may be the same or different and each represents an alkyl group), for instance. The above substituted ammonio group forms a salt with a conjugated base of a monobasic or polybasic inorganic acid or fatty acid. The inorganic acid is not particularly restricted but includes, among others, hydrochloric acid, phosphoric acid, sulfuric acid and nitric acid. The fatty acid is not particularly restricted but includes, among others, formic acid, acetic acid and propionic acid.

In the above general formula (I), Z is preferably —SO$_3$M$^3$ or —SO$_3$M$^4{}_{1/2}$, more preferably —SO$_3$M$^3$, still more preferably —SO$_3$Na.

The fluorine-containing 2-alkoxypropionic acid derivative represented by the above general formula (I) is preferably one in which, in the above general formula (I), Z is —SO$_3$M$^3$, A is —OM$^1$ or —OM$^2{}_{1/2}$, $Y^1$ is a trifluoromethyl group, $Y^2$ is a fluorine atom and m is 2. More preferably, in the above general formula (I), Z is —SO$_3$Na, A is —ONa, X is a fluorine atom, $Y^2$ is a fluorine atom, n is 0 and m is 2.

The method for preparing the fluorine-containing 2-alkoxypropionic acid derivative represented by the above general formula (I) is not particularly restricted but, for example, any of the methods known in the art can be employed. Among the fluorine-containing 2-alkoxypropionic acid derivatives represented by the above general formula (I), those compounds represented by the following general formula:

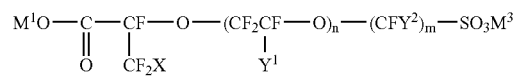

(wherein X, $Y^1$, $Y^2$, n, m, M$^1$ and M$^2$ are as defined above) can be obtained by neutralizing or saponifying the corresponding compounds represented by the following general formula:

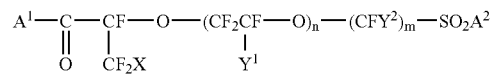

(wherein A$^1$ represents an alkoxyl group or a halogen atom, A$^2$ represents a halogen atom; X, $Y^1$, $Y^2$, n and m are as defined above) using a neutralizing reagent.

The method for producing a water-soluble fluorine-containing vinyl ether according to the present invention comprises subjecting a fluorine-containing 2-alkoxypropionic acid derivative represented by the above general formula (I) to thermal decomposition in the presence of a coordinating organic solvent to give the corresponding water-soluble fluorine-containing vinyl ether represented by the general formula (II).

The coordinating organic solvent has a coordinating property with the ion of the above-mentioned M$^1$ or the ion of the above-mentioned M$^2$. In the method for producing a water-soluble fluorine-containing vinyl ether according to the present invention, the above coordinating organic solvent exhibits a decarboxylation reaction-promoting catalytic action by coordinating the ion of M$^1$ or the ion of M$^2$ which the fluorine-containing 2-alkoxypropionic acid derivative of the above general formula (I) has.

The coordinating organic solvent is not particularly restricted but may be any of those having a coordinating property with an ion of M$^1$ or an ion of M$^2$. Preferably, it comprises an aprotic polar organic solvent. The aprotic polar organic solvent is not particularly restricted but includes, among others, ether solvents, sulfolane, hexamethylphosphoric triamide, acetonitrile, dimethylformamide, dimethyl sulfoxide, ethyl acetate, tetramethylurea and the like. One or two or more of these may be used singly or in combination.

The ether solvent is not particularly restricted but includes, among others, glyme-based compounds, diethyl ethers, diisopropyl ethers, tetrahydrofuran, dioxane, anisole, and crown ethers. These may be used singly or two or more of them may be used in combination.

The above-mentioned glyme-based compounds are hydrocarbon-based ether compounds represented by the general formula:

wherein R represents —$C_pH_{2p+1}$, p represents an integer of 1 to 5 and q represents an integer of 1 to 10.

As the above-mentioned glyme-based compounds, there may be mentioned dimethoxyethane, monoethylene glycol dimethyl ether, diethylene glycol dimethyl ether, triethylene glycol dimethyl ether, tetraethylene glycol dimethyl ether, diethylene glycol monomethyl ether, diethylene glycol monoethyl ether and diethoxyethane, among others. These may be used singly or two or more of them may be used in combination.

The above-mentioned aprotic organic polar solvent is preferably a glyme-based solvent, more preferably diethylene glycol dimethyl ether.

Preferably, the aprotic polar organic solvent has a water content not exceeding 250 ppm so that the yield of the water-soluble fluorine-containing vinyl ether may be increased. The aprotic polar organic solvent is required to have the water content within the above range only at least on the occasion of thermal decomposition. More preferred is diethylene glycol dimethyl ether with a water content not exceeding 250 ppm.

In cases where a low-boiling solvent such as ethyl acetate or tetrahydrofuran is used as the coordinating organic solvent, such equipment as a pressure reaction apparatus becomes necessary for carrying out the thermal decomposition reaction at a temperature not lower than the boiling point of such solvent; however, the purification of the water-soluble fluorine-containing vinyl ether is easier than in the case of using a glyme-based solvent.

In carrying out the thermal decomposition in the practice of the present invention, the coordinating organic solvent itself may be used also as a dispersion medium. It is also possible, however, to use an inert solvent together with the coordinating organic solvent. Preferred as the inert solvent are fluorocarbons, which can be readily dehydrated, so that the yield of the water-soluble fluorine-containing vinyl ether may be increased. The fluorocarbons are not particularly restricted but include, among others, fluorocarbons and fluorochlorocarbons, which may be etherified. Among them, perfluorocarbons and perfluorochlorocarbons are preferred. The inert solvent may comprise one single species or two or more species.

The coordinating organic solvent is used in an amount of 10 to 1,000 parts by mass per 100 parts by mass of the fluorine-containing 2-alkoxypropionic acid derivative. Within the above range, the thermal decomposition initiation temperature becomes low, hence the byproduct formation can be suppressed. When that amount is less than 10 parts by mass, the thermal decomposition reaction may proceed slowly and/or the thermal decomposition may proceed only to an unsatisfactory extent. When the amount exceeds 1,000 parts by mass, a large reaction vessel becomes necessary and this is disadvantageous from the industrial viewpoint. A preferred lower limit is 30 parts by mass, and a preferred upper limit is 300 parts by mass.

The method for producing a water-soluble fluorine-containing vinyl ether according to the present invention is characterized in that the above-mentioned fluorine-containing 2-alkoxypropionic acid derivative is subjected to thermal decomposition at a temperature not lower than 50° C. but lower than 170° C. in the presence of the above-mentioned coordinating organic solvent to give the corresponding water-soluble fluorine-containing vinyl ether represented by the general formula (II).

When the thermal decomposition according to the present invention is carried out at temperatures not lower than 170° C., byproducts are formed in large amounts. The byproducts have not yet been clearly identified but probably are, among others, oligomers represented by the formula:

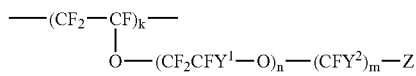

(wherein k represents an integer of 2 to 15, and $Y^1$, $Y^2$, Z, n and m are as defined above) as formed by the reaction of the fluorine-containing 2-alkoxypropionic acid derivative with the water-soluble fluorine-containing vinyl ether or by the mutual reaction of molecules of the water-soluble fluorine-containing vinyl ether. As the byproduct formation increases, the yield of the water-soluble fluorine-containing vinyl ether decreases. In particular, when the reactor size increases, a long time is required for raising and lowering the temperature and, accordingly, the water-soluble fluorine-containing vinyl ether is exposed to high temperatures for a prolonged period of time, with the result that the byproduct formation is still increased.

As for the method of purifying the water-soluble fluorine-containing vinyl ether, recrystallization may be a promising method. Since, however, the byproducts are not crystallizable, it is difficult to crystallize the water-soluble fluorine-containing vinyl ether in the presence of a large amount of such byproducts.

When, in carrying out the thermal decomposition according to the present invention, the temperature is lower than 50° C., time is required for the thermal decomposition or the thermal decomposition may fail to proceed, although the byproduct formation mentioned above can be suppressed. The thermal decomposition is preferably carried out at a temperature not lower than 50° C. but lower than 150° C. Preferably, the thermal decomposition is carried out after thoroughly drying, for dehydration, the fluorine-containing 2-alkoxypropionic acid derivative and catalyst, and the inert solvent to be used if desirable.

The thermal decomposition reaction time in the practice of the present invention is preferably 10 to 600 minutes after arrival at the intended reaction temperature, although it depends on the temperature at which the thermal decomposition is carried out. If the reaction time is shorter than 10 minutes, the thermal decomposition may be incomplete. A more preferred lower limit is 30 minutes, and a more preferred upper limit is 300 minutes.

In the practice of the present invention, the fluorine-containing 2-alkoxypropionic acid derivative preferably has a water content not exceeding 0.1% by mass. When the water content is higher than 0.1% by mass, the fluorine-containing 2-alkoxypropionic acid derivative reacts with the water in certain cases to give, as a byproduct, a compound represented by the general formula:

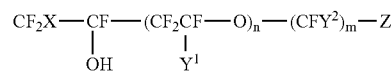

(wherein X, $Y^1$, $Y^2$, Z, n and m are as defined above) and, accordingly, the yield of the water-soluble fluorine-containing vinyl ether tends to decrease. It is only required that the fluorine-containing 2-alkoxypropionic acid derivative has a water content within the above range at least on the occasion of carrying out the thermal decomposition.

The water-soluble fluorine-containing vinyl ether obtained by the method for producing a water-soluble fluorine-containing vinyl ether according to the present invention is represented by the above general formula (II) given herein above. In the above general formula (II), $Y^1$, $Y^2$, Z, n and m are as defined herein above referring to the above general formula (I).

According to the method of the present invention, byproduct formation can be inhibited by subjecting the fluorine-containing 2-alkoxypropionic acid derivatives to thermal decomposition at a temperature not lower than 50° C. but lower than 170° C. using the above-mentioned coordinating organic solvent, therefore the water-soluble fluorine-containing vinyl ethers can be obtained in good yields from the fluorine-containing 2-alkoxypropionic acid derivatives.

The water-soluble fluorine-containing vinyl ethers can be polymerized, either as such or after protection of the terminal hydrophilic group by fluorination or by esterification, amidation or imidation, together with another fluoroolefin, for instance, to give copolymers.

The copolymers obtained, which have salt-forming hydrophilic groups, can be adequately used as electrolyte membranes such as ion exchange membranes or diaphragms. As for the ion exchange membranes, they can be utilized in salt electrolysis, chemical sensors, separation membranes, fuel cells and so forth. The copolymers obtained can also be used as macromolecular superstrong acid catalysts in the form of powders as such, or in lithium cells or the like, in the form of liquids.

BEST MODES FOR CARRYING OUT THE INVENTION

The following examples illustrate the present invention in further detail. These examples are, however, by no means limitative of the scope of the present invention.

PRODUCTION EXAMPLE 1

Synthesis of a Fluorine-Containing 2-alkoxypropionic Acid Derivative 1.1) A 6-liter glass-lined pressure-resistant autoclave was charged with $SO_3$ (2 liters) freshly prepared by distillation of Sulfan (stabilized sulfuric anhydride; product of Nisso Metallochemical Co.), the inside space atmosphere was purged with pure nitrogen gas for substitution therewith, and tetrafluoroethylene was then charged into the autoclave under pressure, upon which the exothermal reaction started immediately. The reaction was continued while maintaining the temperature at 40-60° C. and the pressure at 0.1 to 0.2 MPa. After 40 minutes, when the product amount increased to 5.2 liters and the absorption of tetrafluoroethylne was no longer observed, the reaction was terminated by cooling. The reaction product was a colorless, transparent liquid, which, upon distillation, was found to be almost pure tetrafluoroethane β-sultone.

1.2) A 6-liter glass-lined pressure-resistant autoclave was charged with 400 g of potassium fluoride thoroughly dried at 300° C. and then tightly closed under nitrogen streams. Then, 1 liter of diethylene glycol dimethyl ether was charged into the autoclave, and the sultone (1 liter) obtained in the step 1.1) was added dropwise. A marked exothermic reaction took place, and it was confirmed by $^{19}$F-NMR analysis that the isomerization reaction to $FSO_2CF_2COF$ had been completed almost quantitatively although the formation of free $FSO_2CF_2CF_2OK$ was also observed.

1.3) The product $FSO_2CF_2COF$ obtained using the same reaction apparatus and conditions as used in the step 1.2) was added, under pressure at −10° C., and hexafluoropropylene oxide [HFPO] gas was added to a pressure of 0.2 MPa, whereupon the exothermal reaction started immediately. While the temperature was adjusted to −15 to −5° C., the reaction was continued at a pressure of 0.1 to 0.2 MPa for 3 hours. Thereafter, the rate of pressure dropping decreased, so that the reaction was interrupted, and the residual gas was discharged. The volume of the product was 2.7 liters, and the product consisted of a yellow upper phase and a colorless lower phase. Upon distillation, 90% by volume of the product was found to be the HFPO (one mole) adduct, namely the compound:

$FSO_2CF_2CF_2OCF\,(CF_3)\,COF.$

In addition, the formation of a slight amount of $FSO_2CF_2COF$ and the HFPO (two moles) adducts was observed.

1.4) The compound obtained in the step 1.3) was neutralized with a 20% (by mass) aqueous solution of sodium hydroxide for quantitative conversion to the corresponding fluorine-containing 2-alkoxypropionic acid derivative. Thus was obtained a 36% (by mass) aqueous solution of a compound represented by the formula:

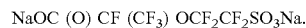

$NaOC\,(O)\,CF\,(CF_3)\,OCF_2CF_2SO_3Na.$

The aqueous solution obtained was removed of the insoluble NaF by filtration and then dried at 80° C. for 36 hours and then further at 120° C. for 12 hours.

EXAMPLE 1

A 20-liter glass vessel equipped with a stirrer was charged with the fluorine-containing 2-alkoxypropionic acid derivative $NaOC(O)CF(CF_3)OCF_2CF_2SO_3Na$ (6.4 kg) obtained in Production Example 1 and 5.3 kg of diethylene glycol dimethyl ether (83 parts by mass per 100 parts by mass of the fluorine-containing 2-alkoxypropionic acid derivative). The vessel was heated by means of a mantle heater. Upon arrival of the inside temperature at 100° C., the generation of $CO_2$ started. The inside temperature was then slowly raised to 140° C. After 180 minutes of heating, the $CO_2$ generation subsided and, therefore, the heating was discontinued. Pure water (6 liters) was added to the reaction mixture obtained for dissolving the same, the insoluble sodium fluoride was filtered off, and the remaining diethylene glycol dimethyl ether layer was extracted with 7 portions of chloroform to give an aqueous solution.

The thus-obtained aqueous solution was subjected to $^{19}$F-NMR spectrometry, and a comparison was made between the large peak at about −83.3 ppm (relative to $CDCl_3$) due to the underlined fluorine atoms of —OC$\underline{F_2}CF_2$— in the water-soluble fluorine-containing vinyl ether $CF_2$=CF—OC$\underline{F_2}CF_2$—$SO_3Na$ and a number of byproduct-due small peaks at −78 to −85 ppm. It was found that the ratio [water-soluble fluorine-containing vinyl ether]:[byproducts] was 100:9. The aqueous solution obtained was evaporated to dryness; the product was readily crystallized and could be purified by recrystallization.

COMPARATIVE EXAMPLE 1

A 20-liter glass vessel equipped with a stirrer and a reflux condenser was charged with 6.4 kg of the fluorine-containing 2-alkoxypropionic acid derivative $NaOC(O)CF(CF_3)OCF_2CF_2SO_3Na$ obtained in Production Example 1 and, as inert solvents, 17.7 kg of Cl(CF$_2$CFCl)$_3$Cl and 240 g of diethylene glycol dimethyl ether (3 parts by mass per 100 parts by mass of the fluorine-containing 2-alkoxypropionic acid derivative). The vessel was heated by means of a mantle heater. Upon arrival of the inside temperature at 180° C., the generation of CO$_2$ started. After 7 hours of heating under refluxing conditions (inside temperature 203° C.), the CO$_2$ generation suppressed and, therefore, the heating was discontinued. After cooling, the reaction mixture obtained was filtered, and the solid matter was washed with HCFC-225. The solid matter thus obtained was dissolved in water, and the insoluble sodium fluoride was filtered off to give an aqueous solution.

The thus-obtained aqueous solution was subjected to $^{19}$F-NMR spectrometry, and a comparison was made between the large peak at about −83.3 ppm (relative to CDCl$_3$) due to the underlined fluorine atoms of —OC$\underline{F}_2$CF$_2$— in the water-soluble fluorine-containing vinyl ether CF$_2$=CF—OC$\underline{F}_2$CF$_2$—SO$_3$Na and a number of byproduct-due small peaks at −78 to −85 ppm. It was found that the ratio [water-soluble fluorine-containing vinyl ether]:[byproducts] was 100:102. The aqueous solution obtained was evaporated to dryness; the product only became a thick syrup-like substance but could not be purified by recrystallization.

EXAMPLE 2

A 500-ml SUS stainless steel autoclave equipped with a reflux condenser was charged with the fluorine-containing 2-alkoxypropionic acid derivative NaOC(O)CF(CF$_3$)OCF$_2$CF$_2$SO$_3$Na (80 g) obtained in Production Example 1 and 130 g of ethyl acetate (163 parts by mass per 100 parts by mass of the fluorine-containing 2-alkoxypropionic acid derivative). The contents were heated to 145° C. by means of a heater and stirred. The CO$_2$ generated was discharged through the reflux condenser so that the autoclave inside pressure might be maintained at a level not exceeding 0.1 MPa. After 5 hours, no increase in inside pressure was observed any longer, so that the autoclave was allowed to cool. All the internal gas was discharged at around room temperature. The reaction mixture was filtered, and the filtrate was concentrated under reduced pressure to give a white solid. The solid obtained was subjected to $^{19}$F-NMR spectrometry, whereby it was confirmed that the water-soluble fluorine-containing vinyl ether CF$_2$=CF—OCF$_2$CF$_2$—SO$_3$Na was the main product ([water-soluble fluorine-containing vinyl ether]:[byproducts] =100:9).

EXAMPLE 3

A 300-ml SUS 316 stainless steel autoclave was charged with 81 g of the fluorine-containing 2-alkoxypropionic acid derivative NaOC(O)CF(CF$_3$)OCF$_2$CF$_2$SO$_3$Na obtained in Production Example 1 and 88 g of tetrahydrofuran (109 parts by mass per 100 parts by mass of the fluorine-containing 2-alkoxypropionic acid derivative). The contents were heated to 140° C. by means of a heater and stirred for 3 hours. The autoclave inside pressure arrived at a maximum of 1.4 MPa. The autoclave was allowed to cool, and all the internal gas was discharged at around room temperature. The reaction mixture was filtered, and the filtrate was concentrated under reduced pressure to give a white solid. The solid obtained was subjected to $^{19}$F-NMR spectrometry, and it was confirmed that the water-soluble fluorine-containing vinyl ether CF$_2$=CF—OCF$_2$CF$_2$—SO$_3$Na was the main product ([water-soluble fluorine-containing vinyl ether]:[byproducts] =100:11).

INDUSTRIAL APPLICABILITY

The method for producing a water-soluble fluorine-containing vinyl ether according to the present invention, which has the constitution described above, makes it possible to obtain water-soluble fluorine-containing vinyl ethers in good yields from the corresponding fluorine-containing 2-alkoxypropionic acid derivatives.

The invention claimed is:

1. A method for producing a water-soluble fluorine-containing vinyl ether which comprises subjecting a fluorine-containing 2-alkoxypropionic acid derivative represented by the following general formula (I):

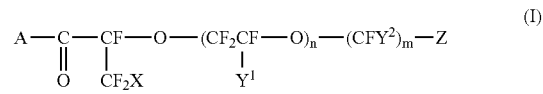

(wherein A represents —OM$^1$ or —OM$^2$$_{1/2}$, and M$^1$ represents an alkali metal and M$^2$ represents an alkaline earth metal; X represents a halogen atom; Y$^1$ and Y$^2$ are the same or different and each represents a fluorine atom, a chlorine atom, a perfluoroalkyl group or a fluorochloroalkyl group; n represents an integer of 0 to 3, and n atoms/groups of Y$^1$ may be the same or different; m represents an integer of 1 to 5, and m atoms/groups of Y$^2$ may be the same or different; and Z represents a hydrophilic group) to thermal decomposition at a temperature of not lower than 50° C. but lower than 170° C. in the presence of a coordinating organic solvent comprising one or both of ethyl acetate and tetrahydrofuran to give a water-soluble fluorine-containing vinyl ether represented by the following general formula (II):

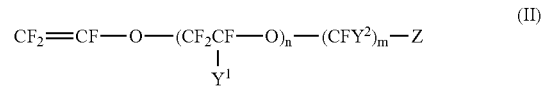

(wherein Y$^1$, y$^2$, Z, n and m are as defined above), said coordinating organic solvent having a coordinating property with an ion of said M$_1$ or an ion of said M$^2$ and said coordinating organic solvent being in an amount of 10 to 1,000 parts by mass per 100 parts by mass of said fluorine-containing 2-alkoxypropionic acid derivative.

2. The method for producing a water-soluble fluorine-containing vinyl ether according to claim 1, wherein the hydrophilic group is —COOM$^3$, —OS0$_3$M$^3$, —SO$_3$M$^3$, —O$_2$PM$^3$, —OP(OM$^3$)$_2$, —O$_2$P(OM$^3$), —OPO(OM$^3$)$_2$, —PO$_2$(OM$^3$), —PO(OM$^3$)$_2$, —COOM$^4$$_{1/2}$, —OSO$_3$M$^4$$_{1/2}$, —OSO$_3$M$^4$$_{1/2}$, —SO$_3$M$^4$$_{1/2}$, —O$_2$PM$^4$$_{1/2}$, —OP(OM$^4$$_{1/2}$)$_2$, —O$_2$P(OM$^4$$_{1/2}$), —OPO(OM$^4$$_{1/2}$)$_2$, —PO$_2$(OM$^4$$_{1/2}$), —PO(OM$^4$$_{1/2}$)$_2$, or a substituted ammonio group forming a salt with a conjugate base of an inorganic acid or fatty acid (its substituents being two or three alkyl groups which are the same or different), wherein M$^3$ represents an alkali metal, a hydrogen atom or NR$^1$R$^2$R$^3$R$^4$ in which R$^1$, R$^2$, R$^3$ and R$^4$ are the same or different and each represents a hydrogen atom or an alkyl group containing 1 to 4 carbon atoms, and M$^4$ represents an alkaline earth metal.

3. The method for producing a water-soluble fluorine-containing vinyl ether according to claim 1,
wherein the thermal decomposition is carried out at a temperature not lower than 50° C. but lower than 150° C.

4. The method for producing a water-soluble fluorine-containing vinyl ether according to claim 1,
wherein the coordinating organic solvent is in an amount of 30 to 300 parts by mass per 100 parts by mass of the fluorine-containing 2-alkoxypropionic acid derivative.

5. The method for producing a water-soluble fluorine-containing vinyl ether according to claim 1,
wherein the coordinating organic solvent comprises an aprotic polar organic solvent.

6. The method for producing a water-soluble fluorine-containing vinyl ether according to claim 5,
wherein the aprotic polar organic solvent is an ether solvent, sulfolane, hexamethylphosphoric triamide, acetonitrile, dimethylformamide, dimethyl sulfoxide, ethyl acetate and/or tetramethylurea.

7. The method for producing a water-soluble fluorine-containing vinyl ether according to claim 6,
wherein the ether solvent is a glyme-based solvent, a diethyl ether, a diisopropyl ether, tetrahydrofuran, dioxane, anisole and/or a crown ether.

8. The method for producing a water-soluble fluorine-containing vinyl ether according to claim 7,
wherein the glyme-based solvent is dimethoxyethane, diethoxyethane, monoethylene glycol dimethyl ether, diethylene glycol dimethyl ether, triethylene glycol dimethyl ether, tetraethylene glycol dimethyl ether, diethylene glycol monomethyl ether and/or diethylene glycol monoethyl ether.

9. The method for producing a water-soluble fluorine-containing vinyl ether according to claim 5, wherein the aprotic polar organic solvent is a glyme-based solvent.

10. The method for producing a water-soluble fluorine-containing vinyl ether according to claim 5,
wherein the aprotic polar organic solvent has a water content not exceeding 250 ppm.

11. The method for producing a water-soluble fluorine-containing vinyl ether according to claim 5,
wherein the aprotic polar organic solvent is diethylene glycol dimethyl ether.

12. The method for producing a water-soluble fluorine-containing vinyl ether according to claim 11,
wherein the diethylene glycol dimethyl ether has a water content not exceeding 250 ppm.

13. The method for producing a water-soluble fluorine-containing vinyl ether according to claim 1,
wherein the fluorine-containing 2-alkoxypropionic acid derivative represented by the general formula (I) has a water content not exceeding 0.1% by mass.

14. The method for producing a water-soluble fluorine-containing vinyl ether according to claim 1,
wherein n is 0 or 1.

15. The method for producing a water-soluble fluorine-containing vinyl ether according to claim 2,
wherein Z is —$SO_3M^3$ or —$SO_3M^4_{1/2}$.

16. The method for producing a water-soluble fluorine-containing vinyl ether according to claim 2,
wherein Z is —$SO_3M^3$, A is —$OM^1$ or —$OM^2_{1/2}$, $Y^1$ is a trifluoromethyl group, $Y^2$ is a fluorine atom and m is 2.

17. The method for producing a water-soluble fluorine-containing vinyl ether according to claim 16, wherein n is 0.

18. The method for producing a water-soluble fluorine-containing vinyl ether according to claim 1,
wherein the coordinating organic solvent comprises at least one solvent with a boiling point not higher than a temperature of the thermal decomposition reaction.

* * * * *